United States Patent [19]
Schuetz

[11] Patent Number: 6,079,876
[45] Date of Patent: Jun. 27, 2000

[54] X-RAY EXPOSURE SYSTEM FOR 3D IMAGING

[75] Inventor: Oliver Schuetz, Erlangen, Germany

[73] Assignee: Siemens Aktiengesellschaft, Munich, Germany

[21] Appl. No.: 09/174,160

[22] Filed: Oct. 16, 1998

[30] Foreign Application Priority Data

Oct. 17, 1997 [DE] Germany .......................... 197 46 096

[51] Int. Cl.[7] .................................................. A61B 6/08
[52] U.S. Cl. .............................. 378/205; 378/4; 378/98.5
[58] Field of Search .................................. 378/205, 206, 378/4, 98.5

[56] References Cited

U.S. PATENT DOCUMENTS

| | | |
|---|---|---|
| 5,109,397 | 4/1992 | Gordon et al. . |
| 5,446,548 | 8/1995 | Gerig et al. ............................ 378/205 |
| 5,512,761 | 4/1996 | Winkelmann . |
| 5,706,324 | 1/1998 | Wiesent et al. . |

FOREIGN PATENT DOCUMENTS

| | | |
|---|---|---|
| 36 04 955 | 8/1987 | Germany . |
| 94 08 562 U | 9/1994 | Germany . |
| 195 35 583 | 3/1997 | Germany . |
| 1 569 885 | 6/1980 | United Kingdom . |

*Primary Examiner*—Craig E. Church
*Attorney, Agent, or Firm*—Hill & Simpson

[57] ABSTRACT

An X-ray system has an X-ray apparatus, an X-ray source and an X-ray receiver on a carrier that is adjustable relative to a subject to be examined for registering 2D projections of a region of the subject from different projection angles with subsequent 3D image reconstruction of the region of the subject, and a position acquisition arrangement having at least one camera allocated to the X-ray apparatus that follows the movements of the X-ray apparatus, and having a position indicator arranged separate from the X-ray apparatus onto which the camera is directed for determining the positions of the X-ray source and the X-ray receiver and for determining the different projection angles of the 2D projections for the 3D image reconstruction. The camera and the position indicator are arranged outside the X-ray beam emanating from the X-ray source.

9 Claims, 4 Drawing Sheets

X-RAY EXPOSURE SYSTEM FOR 3D IMAGING

BACKGROUND OF THE INVENTION

1. Field of the Invention

The present invention is directed to an X-ray system of the type having an X-ray apparatus carrying an X-ray source and an X-ray receiver that are adjustable relative to a subject to be examined for registering 2D projections of a region of the subject from different projection angles, with subsequent 3D image reconstruction of the subject, and is also directed to an apparatus for the determination of the projection geometries.

2. Description of the Prior Art

X-ray systems of the above type have a C-arm for mounting the X-ray source and the X-ray receiver, this C-arm being seated such in a holder at the X-ray system so that it is motor-adjustable in a specific angular range along its circumference (orbital motion). For acquiring 2D projections from different projection angles for 3D image reconstruction of, for example, a body region of a subject using the C-arm X-ray apparatus, the C-arm—after appropriate placement relative to the subject to be examined—is adjusted along its circumference during the registration of 2D projections of the body region of the subject. 3D images of the body region of the subject are subsequently reconstructed from the 2D projections registered with the X-ray system during the adjustment motion of the C-arm. The 3D reconstruction, however, assumes exact knowledge of the projection geometry, i.e. the knowledge of the position of the X-ray source and the X-ray receiver as well as of the projection angle during the registration of each of the individual 2D projections.

In known stationary X-ray systems and in particular, mobile C-arm X-ray systems, mechanical instabilities occur particularly relating to the adjustment of the C-arm along its circumference, causing deviations of the real adjustment motion of the C-arm from the ideal adjustment motion to occur that make the determination of the projection geometries more difficult.

The following two methods are known for determining the projection geometries.

German OS 195 12 819 discloses the employment of a marker ring, usually formed of plexiglass with inserted metal structures, that is arranged around the body region of the subject to be examined. The metal structures of the marker ring are visible in the 2D projections of the body region to be examined, so that the respective projection geometries of the 2D projections can be calculated from their position. This method, however, has the disadvantage that the marker ring has a relatively large diameter, so that the spacing between X-ray source and the marker ring is very small (a few centimeters) given C-arms with a small diameter. The metal structures are therefore appear greatly enlarged in the 2D projections, so that large parts of the 2D projections are overlaid by the metal structures. Further, only a small region of the metal structures of the marker ring is imaged in the 2D projections, so that the determination of the projection geometries is difficult on the basis of the small number of imaged metal structures.

Calibration measurements can be made before the actual patient measurement, assuming that the system behavior, i.e. essentially the adjustment motions of the C-arm, is reproducible to a high degree. This method, however, is extremely time-consuming and, moreover, can only be applied given a mechanically reinforced, stationary C-arm X-ray apparatus. Application to mobile X-ray apparatus is not possible because of the aforementioned mechanical instability of such an X-ray apparatus. Similar mechanical stabilization is precluded for a mobile X-ray apparatus because of the great increase in weight that would result, which would limit the mobility.

U.S. Pat. No. 5,109,397 discloses a mobile computed tomography system having an X-ray system rotating around a rotation center and including an X-ray source and an X-ray receiver to which sensors are allocated, these sensors moving along with the X-ray system and interacting with a stationary ring allocated to the rotation center for detecting lateral movements of the X-ray system during a scan. The sensors generate signals which are evaluated to determine the spacings between their defined point of attachment and the ring. The acquired data are subsequently utilized in the reconstruction of tomograms. The ring is arranged in the propagation path of an X-ray beam emanating from the X-ray source.

Sensors for determining the distance of two objects from one another are also disclosed in German PS 43 32 254 and German Utility Model 94 08 562. The determination of the distance thereby ensues by measuring the transit time of acoustic waves or electromagnetic waves.

British Specification 1 569 885 describes a computed tomography system with an X-ray apparatus rotating around a rotation center that includes components for determining the projection geometries of the X-ray system during a scan. The components are arranged outside the beam path of the X-ray beam of the X-ray system and include a light source, a photocell and a ring with opaque marks that interact with the light from the light source such that light pulses are generated given rotations of the X-ray system. The projection angles during a scan are determined for the image reconstruction on the basis of the light pulses.

German OS 36 04 955 discloses an X-ray diagnostics apparatus having an image generating system with X-ray radiator and a radiation receiver as well as a patient table. Position sensors in the form of potentiometers that acquire the position of adjustable components of the image generating system are connected to these components.

German OS 195 35 583 also discloses an X-ray diagnostic apparatus with a positioning aid. A light transmitter for emitting a light beam is provided such at an X-ray image intensifier so that this light beam is focused onto a X-ray radiator lying opposite the X-ray image intensifier. In this way, a positioning of the X-ray radiator and X-ray image intensifier can ensue with reference to an examination subject without emitting X-rays.

SUMMARY OF THE INVENTION

An object of the present invention is to provide an X-ray system of the type initially described wherein the determination of the projection geometries is simplified, and which can be utilized stationary as well as mobile.

This object is inventively achieved in an X-ray system having an X-ray apparatus carrying an X-ray source and an X-ray receiver that are adjustable relative to a subject to be examined for registering 2D projections of a region of the subject from different projection angles with subsequent 3D image reconstruction of the region of the subject, and a position acquisition arrangement having at least one camera mechanically allocated to the X-ray apparatus that follows the movements of the X-ray apparatus, and having a position indicator which is separate from the X-ray apparatus and which is in the field of view of the camera and which produces data in the image (signals) from the camera from which the positions of the X-ray source, the X-ray receiver, and the different projection angles of the 2D projections for the 3D image reconstruction are determined. The camera and the position indicator are arranged outside the X-ray beam emanating from the X-ray source. In the inventive system the determination of the projection geometries is simplified compared to known systems, wherein the arrangement for acquiring position geometries is disposed in the x-ray beam, by the arrangement of the camera and the position indicator of the position acquisition system such they are not within the X-ray beam emanating from the X-ray source. The inventive apparatus thus avoids the aforementioned problems with having to evaluate items in the X-ray image itself for the determination of the projection geometry in each 2D projection. As a further result, moreover, the precision of the determination of the projection geometries is also improved since the determination of the projection geometries on the basis of the camera and the position indicator is not based, as it is in the known apparatus, on the evaluation of small structures of the apparatus imaged in the 2D projections.

Because neither the camera nor the position indicator is imaged in the 2D projections, moreover, no superimpositions of X-ray-positive structures with the region of the subject to be examined and displayed occur in the 2D projections. In this way, the reconstruction of a 3D image of the subject from the registered 2D projections that is free of structures foreign to the body is simplified. Moreover, the camera and the arrangement for the determination of the projection geometries are suitable for mobile as well as stationary X-ray systems, with mechanical instabilities of the X-ray apparatus given the adjustment of the X-ray system being insignificant for the determination of the projection geometries.

The determination of the projection angles on the basis of the evaluation of camera images, i.e. independent of direct, for example electro-mechanical, or indirect, for example electro-optical, distance measurements also offers the advantage that disturbances such as wearing at mechanical components or unwanted electrical signals cannot degrade the exact determination of the projection angles.

In a preferred embodiment of the invention, at least one camera is arranged at each of the X-ray source and the X-ray receiver, each of these cameras being respectively directed onto the position indicator, which can be a marker ring according to one version of the invention. The marker ring according to the invention differs from the known marker rings because it does not comprise any X-ray positive structures for the determination of the projection geometries. The marker ring according to the invention can be completely fabricated of an X-ray positive material, for example stainless steel. The cameras arranged at the X-ray source and the X-ray receiver, these cameras being co-moved with those components during the adjustment motion of the X-ray apparatus, are directed onto the stationary marker ring so that the positions of the X-ray source and of the X-ray receiver can be identified in a stationary coordinate system, for example a Cartesian coordinate system, on the basis of camera exposures of the circumference of the marker ring that are synchronized with the registration of 2D projections. The position of the stationary marker ring in the stationary coordinate system and the position of the cameras relative to the X-ray source and the X-ray receiver are thereby known. The appertaining projection angles of the 2D projections for the 3D image reconstruction can be determined on the basis of the positions of the X-ray source and the X-ray receiver in the coordinate system identified for each 2D projection.

In a further version of the invention, the marker ring is provided with defined, i.e. periodic, uniformly distributed, surface structures along its circumference. The registration of the surface structures of the marker ring with the camera simultaneously with a registration of a 2D projection enables an unambiguous identification of the positions of the X-ray source and the X-ray receiver relative to the marker ring, and thus the determination of the projection angle belonging to the 2D projection. A more coarse determination of the projection angles, moreover, can also ensue on the basis of position sensors mounted on the X-ray apparatus, followed by the fine determination of the projection angles in which the surface structures of the marker ring recorded by the cameras are analyzed. It then suffices to fashion the surface structures of the marker ring differently at angular spacings in a range of approximately 30° through 40° that are periodically repeated over the entire circumference of the marker ring.

According to another version of the invention, the marker ring is provided with electrically operated, optically active elements at defined locations along its circumference. In a further version of the invention the marker ring is provided with infrared light sources and/or passive infrared elements that are illuminated, for example, with infrared light sources arranged at the cameras and which reflect the infrared light, these active or passive elements being arranged in a defined manner along the circumference of the marker ring. By registering the elements and/or the infrared light sources and/or the illuminated infrared elements arranged in defined fashion with the camera simultaneously with the registration of 2D projections, an unambiguous determination of the projection geometries at the point in time of each and every one of the 2D projections is also possible from their arrangement along the circumference of the marker ring. The periodic arrangement of the elements, or the infrared light sources or the infrared elements along the circumference of the marker ring can ensue analogously to the aforementioned surface structures. The employment of infrared light sources, of course, assumes the employment of corresponding infrared-sensitive cameras.

In a preferred embodiment of the invention the marker ring is formed by separable and joinable ring segments. This is especially advantageous when, according to a further version of the invention, one of these ring segments is arranged at a patient support accepts the examination subject. In this case, the other ring segment is always placed onto this one ring segment only when there is the intent to prepare a series of 2D projections of a region of the subject arranged on the patient support. Otherwise, the other ring segment is removed, so that it does not have a disturbing effect for other examinations and the patient support is freely accessible.

The determination of the projection angles, moreover, is also possible with transmission or reception devices arranged in a spatially defined manner relative to one another at the X-ray source and the X-ray receiver that collaborate with reception or transmission devices arranged in a spatially defined manner relative to one another. For example, a number of spatially defined reception devices, i.e. their position relative to one another is known, attached to a stationary part of the X-ray system, such as distributed over the circumference of the marker ring. At least two transmission devices that are respectively co-moved with the X-ray source and the X-ray receiver during the course of an adjustment motion can be arranged, for example at the X-ray source and at the X-ray receiver so as to be defined relative to one another. According to a version of the invention, the transmission devices—simultaneously with the registration of a 2D projection—emit signals, preferably acoustic waves, such as ultrasound waves, or electromagnetic waves, such as light waves or microwaves, which are received by the reception devices for use in the determination of the projection geometries in various 2D projections. The evaluation of the received ultrasound waves, light waves or microwaves subsequently enables the determination of the exact position of the X-ray source and of the X-ray reception means during each and every 2D projection, so that the projection angles of each of the 2D projections can be calculated from the respectively determined positions of the X-ray source and the X-ray receiver. The phases and/or transit times of the ultrasound waves, light waves or microwaves between transmission and reception devices are preferably identified and evaluated.

DESCRIPTION OF THE PREFERRED EMBODIMENTS

Figure 1:
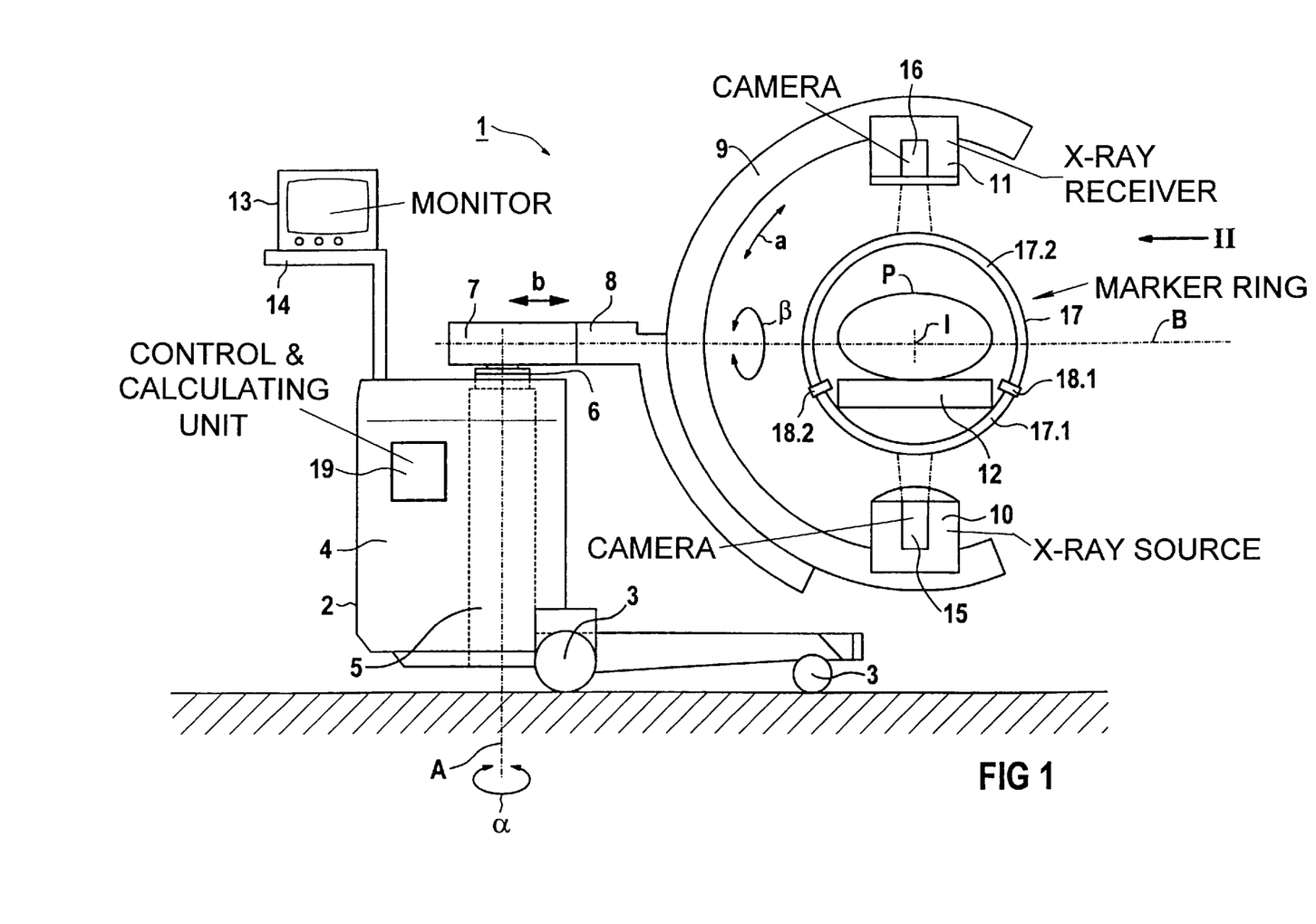
FIG. 1 shows an inventive X-ray system in the form of a mobile C-arm X-ray apparatus with a position acquisition system.

FIG. 1 shows an inventive X-ray system 1 with a C-arm X-ray apparatus 2. The C-arm X-ray apparatus 2 has a cart 4 provided with wheels 3. The C-arm X-ray apparatus 2 is provided with a lifting mechanism 5 that is only schematically indicated in FIG. 1 and has a column 6 with a longitudinal axis A around which the column 6 can be turned in the direction of the double arrow α. A holder 7 is arranged at the column 6, a mount 8 for supporting a C-arm 9 with an isocenter I being in turn arranged at the holder 7. The C-arm 9 carries an X-ray source 10 and an X-ray receiver 11 lying opposite one another at its two ends, arranged relative to one another so that a central ray of an X-ray beam emanating from the X-ray source 10 strikes the X-ray receiver 11 approximately centrally. In a known way, the C-arm 9 is seated at the mount 8 so as to be adjustable motor-driven in the direction of the double arrow a along its circumference in a way not shown in greater detail. In a known way, the mount 8 is rotatable around a common axis B of the holder 7 and the mount 8 (see the double arrow β, angulation) and is seated at the holder 7 so as to be displaceable in the direction of the axis B (see double arrow b). With the assistance of the lifting device 5, the C-arm 9, which is connected to the column 6 of the lifting device 5 via the mount 8 and the holder 7, is vertically adjustable relative to the cart 4.

In the exemplary embodiment, the C-arm X-ray apparatus 2 is provided for producing 3D images of a body region of a patient P (only schematically shown in the figures) lying on a patient bed 12. The 3D images are reconstructed from 2D projections of the body region from different projection directions that are acquired by the X-ray system with the X-ray source 10 and the X-ray receiver 11 and can be displayed with a monitor 13 that is arranged on a holder 14 of the C-arm X-ray apparatus 2.

For registering 2D projections from different projection angles, the C-arm 9 is motor-adjusted along its circumference in the direction of the double arrow a in an angular range of approximately 200° around the body region of the patient P to be examined and visually displayed, with approximately 50 through 100 2D projections of the body region of the patient P being registered from different projection angles.

Figure 2:
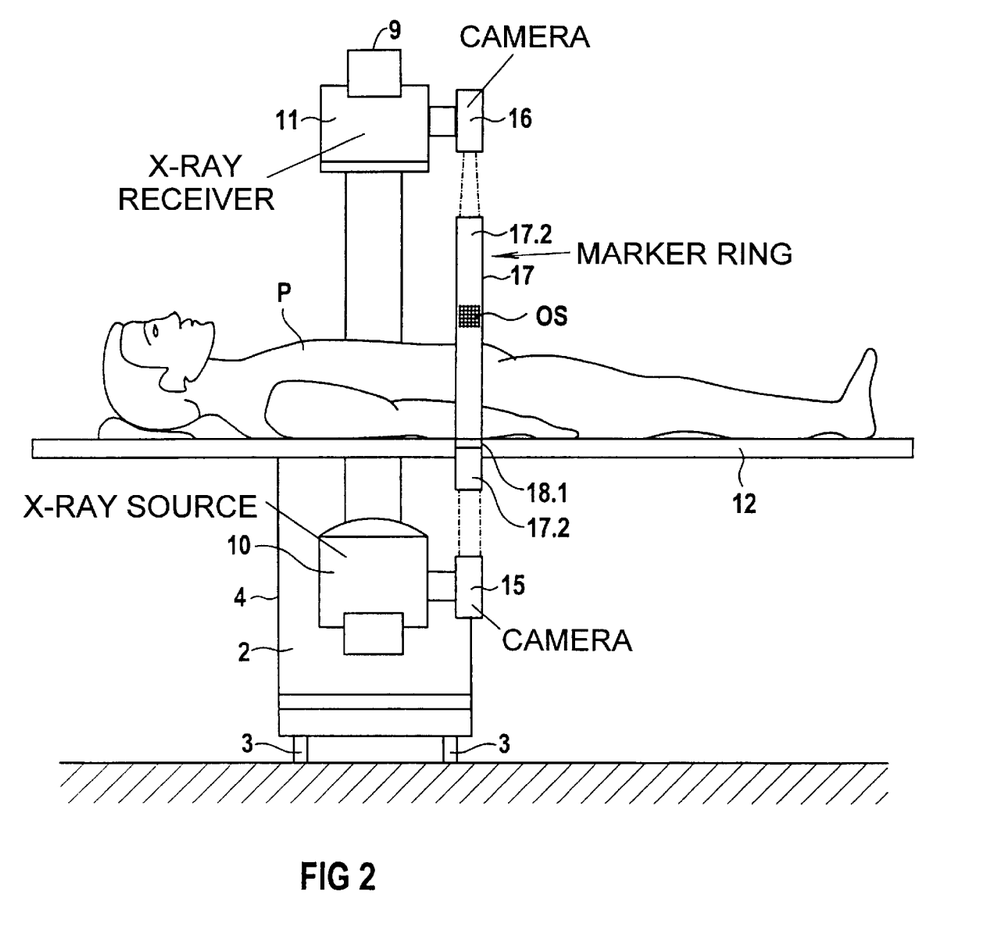
FIG. 2 is a view in the direction of the arrow II of FIG. 1.

For the exact determination of the different positions of the X-ray source 10, of the X-ray receiver 11 and the appertaining projection angles given successive 2D projections, which are absolutely necessary for the 3D image reconstruction of the body region of the patient from the 2D projections, the X-ray source 10 is provided with a laterally arranged camera 15 (see FIG. 2), the X-ray receiver 11 is provided with a laterally arranged camera 16 (see FIG. 2), and the patient bed 12 is provided with a marker ring 17. The cameras 15 and 16 and the marker ring 17 are parts of a position acquisition system.

The marker ring 17 is formed by two ring segments 17.1 and 17.2 that can be joined to or separated from one another at points 18.1, 18.2. The ring segment 17.1 is secured to rails (not shown in greater detail in FIG. 1) that are present at both sides of the patient bed 12 and is displaceable along the rails. When a series of 2D projections of a body region of the patient P is to be registered, the ring segment 17.2 is joined to the ring segment 17.1 at the points 18.1, 18.2, so that the marker ring 17 surrounds the patient P. The marker ring 17 has defined, i.e. systematically generated, surface structures OS (only schematically indicated in FIG. 2) along its circumference. An unambiguous identification of a position with reference to the circumference of the marker ring 17 is possible on the basis of the surface structures OS.

During the course of the registration of a series of 2D projections of a body region of a patient P with subsequent 3D image reconstruction, the C-arm X-ray apparatus 2 is correspondingly positioned relative to the body region of the patient P to be examined. The marker ring 17 is displaced along the rails of the patient bed 12 relative to the cameras 15, 16 arranged at the X-ray source 10 and at the X-ray receiver 11 with the cameras 15, 16 directed onto the circumference of the marker ring 17. In this way, the cameras 15, 16 can register the surface structures OS of the marker ring 17 lying in the respective fields of view of the cameras 15, 16 (see the dot-dash lines in FIG. 2). The position of the camera 15 relative to the X-ray source 10, the position of the camera 16 relative to the X-ray receiver 11 and the position of the marker ring 17 are known in a stationary coordinate system, for example a Cartesian coordinate system, provided for indicating the positions of the X-ray source 10 and of the X-ray receiver.

The image signals of the cameras 15, 16 are supplied to a control and calculating unit 19 of the C-arm X-ray apparatus 2. The control and calculating unit 19, which triggers both the motorized adjustment motion of the C-arm 9 as well as the exposure of 2D projections, also interprets the camera images of the cameras 15, 16 recorded at the point in time of each and every 2D projection. On the basis of the respective settings of the cameras 15, 16 and the registered surface structures OS of the marker ring, the control and calculating unit 19 determines the spacings of the X-ray source 10 and the X-ray receiver 11 from and their orientation relative to the marker ring 17. Since the control and calculating unit 19 knows the position of the marker ring 17 in the Cartesian coordinate system as well as the position of the camera 15 relative to the X-ray source 10 and the position of the camera 16 relative to the X-ray receiver 11, the control and calculating unit 19 can determine the exact position of the X-ray source 10 and the X-ray receiver 11 and the appertaining projection angle with reference to the marker ring for each 2D projection on the basis of the identified spacings and orientations. For example, the identified positions are indicated with respect to the stationary Cartesian coordinate system in which, as already mentioned, the position of the marker ring 17 is known.

The marker ring 17 is preferably formed of a material resistant to deformation, for example stainless steel, and is sterilizeable for use in operating rooms.

A coarse determination of the orientation of the X-ray source 10 and the X-ray receiver 11 relative to the marker ring 17, moreover, ensues on the basis of position sensors (not shown in FIG. 1) of the X-ray apparatus allocated to the C-arm 9, whereas the fine determination ensues on the basis of the evaluation of the cameras exposures of the surface structures OS of the marker ring 17. Accordingly, it suffices to distribute the surface structures OS of the marker ring at spacings, for example, of an angular range of only 30° to 40°. These surface structures OS then repeat periodically over the entire circumference of the marker ring 17. The marker ring 17 can also be provided with surface structures OS that are different from one another over the entire circumference of the marker ring 17.

In this way, thus, the corresponding positions of the X-ray source 10 and the X-ray receiver 11, and thus the respective projection angle, can be determined for every 2D projection. The signal lines for the transmission of the control signals for the motorized adjustment of the C-arm 9, the triggering of 2D projections and the transmission of the camera signals, moreover, are not shown in the figures.

Figure 3:
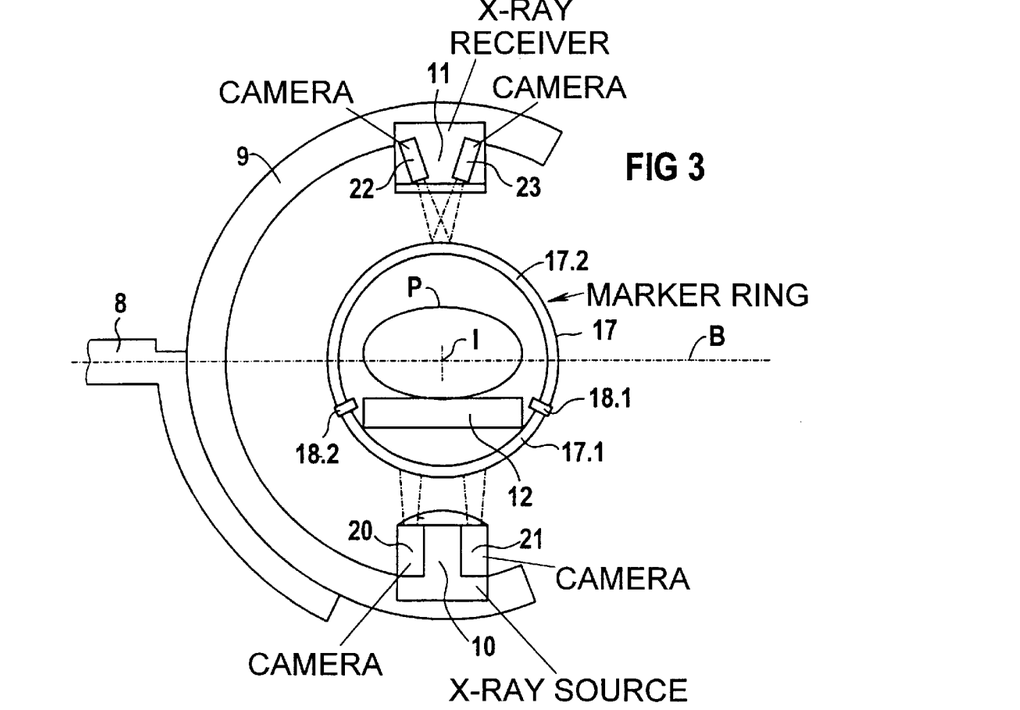
FIG. 3 shows a portion of a second embodiment of the inventive X-ray system.

FIG. 3 shows a portion of a second embodiment of the inventive X-ray means, wherein components of the X-ray system shown in FIG. 3 that are basically identical to components of the X-ray system shown in FIG. 1 are provided with the same reference characters.

In this embodiment, the X-ray source 10 and the X-ray receiver 11 are each provided with two cameras. The cameras 20, 21 are arranged at the X-ray source 10 so that the respective regions of the marker ring 17 covered by the cameras 20, 21 lie as far apart from one another as possible. The cameras 22, 23, by contrast, are arranged such at the X-ray receiver 11 so that approximately the same region of the circumference of the marker ring 17 is covered by the cameras (photogammetric method). The arrangement of the cameras 20 through 23 at the X-ray source 10 and the X-ray receiver 11 is selected such that the precision of the position determination of the X-ray source 10 and the X-ray receiver 11 and the appertaining projection angles is improved on the basis of the additionally acquired information. The cameras 20, 21 can thereby also be arranged relative to one another like the cameras 22, 23. Likewise, the cameras 22, 23 can be arranged relative to one another like the cameras 20, 21.

Figure 4:
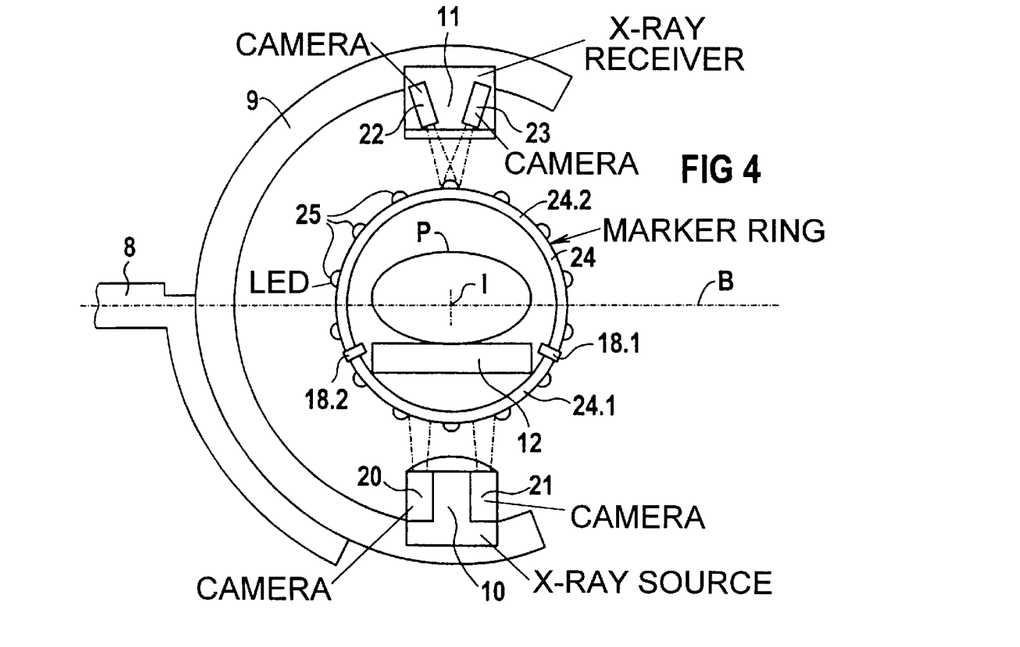
FIG. 4 shows a portion of a third embodiment of the inventive X-ray system.

FIG. 4 shows a portion of a third embodiment of the inventive X-ray system wherein, differing from the second embodiment of the X-ray system, the marker ring 17 is replaced by a marker ring 24. Along its circumference, the marker ring 24 is provided with electrically operated, optically active elements arranged in defined fashion that reside in a defined, geometrically unambiguous relationship relative to one another. The optically active elements can, for example, be light-emitting diodes 25. As in the previously described exemplary embodiment, the cameras 20 through 23 record the structure of the optically active elements on the circumference of the marker ring 24 at the point in time of each and every 2D projection, given a series of 2D projections. As in the way previously described, the control and calculating unit 19 (not shown in FIG. 4) determines the positions of the X-ray source 10 and the X-ray receiver 11 from and their orientation to the marker ring 24 for each 2D projection on the basis of the respective settings (known positions) of the cameras 20 through 23 and the registered signals identifying the optically active elements on the circumference of the marker ring 24. Since, as in the previously described exemplary embodiment, the control and calculating unit 19 knows the position of the marker ring 24 in the Cartesian coordinate system as well as the position of the cameras 20, 21 relative to the X-ray source 10 and the position of the cameras 22, 23 relative to the X-ray receiver 11, the control and calculating means 19 can determine the exact positions of the X-ray source 10 and the X-ray receiver 11 as well as the appertaining projection angles in the Cartesian coordinate system on the basis of the spacings and orientations identified for each 2D projection. The projection geometries identified in this way are then utilized for the reconstruction of 3D images of body regions of the patient P with the control and calculating unit 19, whereby the 3D images, as already mentioned, can be displayed on, for example, the monitor 13 of the C-arm X-ray apparatus 2.

Instead of light-emitting diodes 25, moreover, infrared light sources and/or passive infrared elements that reflect infrared light and are illuminated by, for example, infrared light sources arranged at the cameras 20 through 23 can also be provided over the circumference of the marker ring 24. If infrared light sources are employed, however, appropriate infrared-sensitive cameras for registering the infrared signals are used instead of the cameras 20 through 23.

If expedient, electrically operated, optically active elements can also be combined with infrared light sources and passive infrared elements along the circumference of the marker ring 24.

Like the marker ring 17, moreover, the marker ring 24 is formed by two ring segments 24.1 and 24.2 that can be joined to or separated from one another at points 18.1 and 18.2, with the ring segment 24.1 being secured to rails (not shown in detail in FIG. 4) of the patient bed 12. In a way that is not shown, the marker ring 24 is electrically contacted for supplying the light-emitting diodes 25 with energy.

Figure 5:
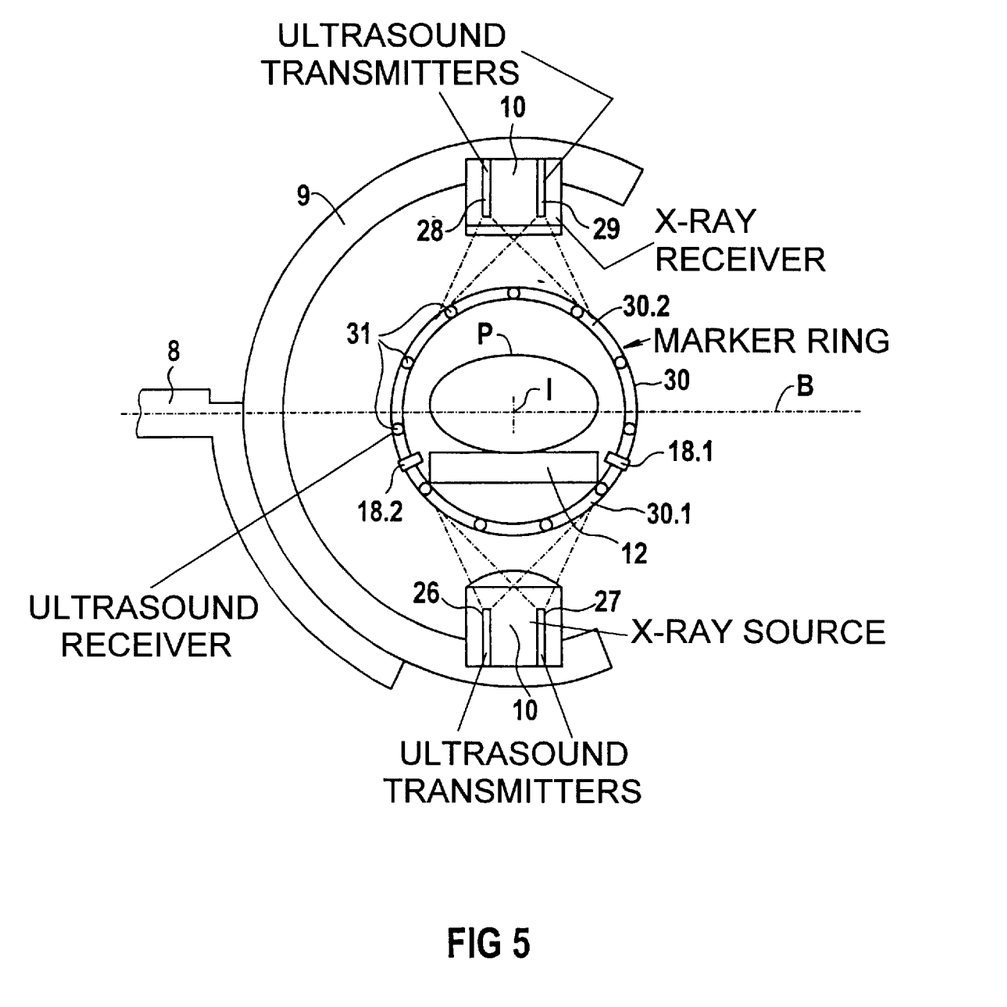
FIG. 5 shows a portion of another possibility of determining projection angles in accordance with the invention.

FIG. 5 shows a portion of another embodiment for determining projection angles. Differing from the above-described embodiments, the cameras arranged at the X-ray source 10 and the X-ray receiver 11 are replaced by transmission devices 26, 27 and 28, 29 arranged in a spatially defined manner relative to one another, and the marker ring 24 is replaced by a marker ring 30 provided with reception devices 31 arranged in a spatially defined manner relative to one another. In the present instance, the transmission devices are ultrasound transmitters 26 through 29 and the reception devices are ultrasound receivers 31. Whereas the ultrasound receivers 31 arranged at the marker ring 30 are stationary with reference to the X-ray system, the ultrasound transmitters 26 through 29 are co-moved with the X-ray system given the adjustment motion of the C-arm 9 along its circumference.

The control and calculating unit 19 (not shown in FIG. 5), which both controls the motorized adjustment of the C-arm 9 and triggers the exposure of 2D projections in the previously described exemplary embodiment, also controls the triggering of emission ultrasound waves by the ultrasound transmitters 26 through 29, which ensues simultaneously with the triggering of a 2D projection. In this way, the corresponding positions of the X-ray source 10 and the X-ray receiver 11, and thus the respective projection angle, can be determined for each 2D projection.

The ultrasound transmitters 26 through 29 are preferably operated at different frequencies, so that the ultrasound waves received by the ultrasound receivers 31 can be unambiguously allocated to one of the ultrasound transmitters 26 through 29.

If the ultrasound transmitters 26 through 29 do not simultaneously emit ultrasound waves given triggering of a 2D projection, but instead emit ultrasound in short, defined time intervals following one another, the ultrasound transmitters 26 through 29 can also be operated at the same transmission frequency, so that the ultrasound waves received by the ultrasound receivers 31 can also be unambiguously allocated to one of the ultrasound transmitters 26 through 29 in this case.

The ultrasound transmitters 26 through 29 and the ultrasound receivers 31 preferably exhibit directional characteristics matched to the adjustment motion of the X-ray system. In this way, the reception of foreign signals on the part of the ultrasound receivers 31 that disturb the signal evaluation can be reduced, and the required transmission power of the ultrasound transmitters 26 through 29 can be reduced compared to isotropically emitting ultrasound transmitters.

For exactly determining the respective positions of the X-ray source 10 and the X-ray receiver 11 in 2D projections relative to a stationary coordinate system, for example a Cartesian coordinate system, preferably at least three of the ultrasound receivers 31 should respectively receive ultrasound waves from the ultrasound transmitters 26 through 29 allocated to the X-ray source 10 and the X-ray receiver 11 during the adjustment motion of the C-arm 9, i.e. an ultrasound wave emitted, for example, by the ultrasound transmitter 29 should be received by at least three ultrasound receivers.

The ultrasound waves received by the ultrasound receivers 31 are subsequently supplied to the control and calculating unit 19 that determines the phases and/or the transit times of the respective ultrasound waves belonging to a 2D projection. Since the transit time of the ultrasound is dependent on the ambient temperature, a unit (not shown in the figures) for measuring the ambient temperature, which is taken into consideration in compensation calculations in the determination of the running time of the ultrasound, can be connected to the control and calculating unit 19.

On the basis of the phase and/or transit time information of the received ultrasound waves, the control and calculating unit 19 calculates the spacing for each ultrasound transmitter 26 through 29 from the ultrasound receivers 31 that have received ultrasound waves emitted by the respective ultrasound transmitters 26 through 29 for each 2D projection. Since the control and calculating unit 19 knows the position of the marker ring 17 or of the ultrasound receivers 31 in the Cartesian coordinate system as well as the position of the ultrasound transmitters 26, 27 relative to the X-ray source 10 and the position of the ultrasound transmitters 28, 29 relative to the X-ray receiver 11, the exact position and the projection angles of the X-ray source 10 and of the X-ray receiver 11 with reference to the stationary coordinate system can be exactly determined for each 2D projection by the control and calculating unit 19 on the basis of the identified spacings for each 2D projection.

The ultrasound transmitters need not necessarily be arranged at the X-ray source 16 and the X-ray receiver 11 and the ultrasound receivers at the marker ring 17. Alternatively, the ultrasound transmitters can be arranged at the marker ring 17 and the ultrasound receivers at the X-ray source 10 and the X-ray receiver.

If only one ultrasound transmitter is provided at each of the X-ray source 10 and at the X-ray receiver 11, at least three of the ultrasound receivers 31 must receive ultrasound waves from the ultrasound transmitters 26 through 29 allocated to the X-ray source 10 and the X-ray receiver 11 during the adjustment motion of the C-arm 9 for exact position determination.

For exact position determination of the X-ray source 10 and the X-ray receiver, however, more than two ultrasound transmitters can also be provided at the X-ray source 10 and the X-ray receiver 11, their ultrasound waves being received by at least one of the ultrasound receivers 31.

The number of ultrasound transmitters and ultrasound receivers provided for the position determination of the X-ray source 10 and the X-ray receiver 11 can thus deviate from the number employed in the present exemplary embodiment. Further, the attachment of the ultrasound transmitters and ultrasound receivers is only described as an example and can also be implemented differently.

Further, the marker ring 30, like the marker rings 17, 24, is also composed of two separable and joinable ring segments 30.1, 30.2 and is correspondingly arranged at the patient bed 12. In a way that is not shown, the marker ring 30 is electrically contacted for the energy supply of the ultrasound receivers 31 and for the signal transmission.

Transmitters and receivers that operate on the basis of other acoustic waves or electromagnetic waves, for example microwaves or light, can be provided for the determination of the projection geometries of the X-ray source 10 and the X-ray receiver 11 instead of the ultrasound transmitters 26 through 29 and the ultrasound receivers 31.

In this case, too, the determination of the projection geometries is based on the determination of phase and/or transit times of microwaves or light waves between transmission devices and reception devices. As in the use of ultrasound, the spacings between transmission and reception devices can be determined on the basis of the phase and/or transit time information, and thus the exact positions and orientations of the X-ray source 10 and the X-ray receiver 11 relative to the marker ring 17 can be determined in every 2D projection. If light waves are employed for determining the projection geometries, laser diodes, light-emitting diodes or super-luminescent diodes are suitable as optical signal sources, and diodes or avalanche photodiodes are available as optical detectors arranged on the marker ring 17.

The inventive X-ray system was explained herein with reference to the example of a mobile C-arm X-ray apparatus 2. The employment of the position acquisition system for the position determination of the X-ray source 10 and the X-ray receiver 11, however, is not limited to use in a mobile C-arm X-ray apparatus but is also possible in a stationary X-ray apparatus.

Although modifications and changes may be suggested by those skilled in the art, it is the intention of the inventor to embody within the patent warranted hereon all changes and modifications as reasonably and properly come within the scope of his contribution to the art.

I claim as my invention:

1. An X-ray system comprising:

an X-ray source which emits an X-ray beam;

an X-ray receiver on which said X-ray beam is incident;

means for moving said X-ray source and said X-ray receiver relative to an examination subject for obtaining a plurality of 2D projections of a region of the subject from a plurality of different projection angles, each of said projection angles having a unique projection geometry of the X-ray source and the X-ray receiver associated therewith, said X-ray source, said X-ray receiver and said means for moving comprising an X-ray apparatus;

a camera allocated to said X-ray apparatus for following movements of said X-ray apparatus, said camera having a field of view and producing camera signals;

a position indicator disposed separate from said X-ray apparatus and in said field of view of said camera, said position indicator producing information in said camera signal identifying the projection geometry for each of said different projection angles of said 2D projections, said camera and said position indicator being disposed outside of said X-ray beam emitted by said X-ray source; and computer means supplied with said camera signals for identifying the different projection angles of the 2D projections and for reconstructing a 3D image therefrom.

2. An X-ray system as claimed in claim 1 comprising a first camera mounted at said X-ray source and a second camera mounted at said X-ray receiver, said first and second cameras having respective fields of view in which said position indicator is disposed, and said first and second cameras supplying respective camera signals to said computer means each containing information identifying said projection geometries.

3. An X-ray system as claimed in claim 1 wherein said position indicator comprises a marker ring.

4. An X-ray system as claimed in claim 3 wherein said marker ring has a circumference, and comprises a plurality of defined surface structures distributed along said circumference.

5. An X-ray system as claimed in claim 3 wherein said marker ring has a circumference and comprises a plurality of electrically operated, optically active elements distributed along said circumference.

6. An X-ray system as claimed in claim 5 wherein said optically active elements comprise a plurality of infrared light sources.

7. An X-ray system as claimed in claim 5 wherein said optically active elements comprise a plurality of passive infrared reflectors illuminated by a plurality of infrared light sources.

8. An X-ray system as claimed in claim 3 wherein said marker ring comprises two separable and joinable ring segments.

9. An X-ray system as claimed in claim 8 further comprising a patient bed adapted for receiving said subject, and wherein one of said two separable and joinable ring segments is mounted at said patient bed.

* * * * *